US008690771B2

(12) United States Patent
Wekell et al.

(10) Patent No.: US 8,690,771 B2
(45) Date of Patent: Apr. 8, 2014

(54) TRENDING DISPLAY OF PATIENT WELLNESS

(75) Inventors: William Wekell, Maple Valley, WA (US); Ken Bevins, Monroe, WA (US); Robert Boyer Koenig, Redmond, WA (US)

(73) Assignee: Spacelabs Healthcare, LLC, Issaquah, WA (US)

( * ) Notice: Subject to any disclaimer, the term of this patent is extended or adjusted under 35 U.S.C. 154(b) by 944 days.

(21) Appl. No.: 11/365,196

(22) Filed: Mar. 1, 2006

(65) Prior Publication Data

US 2006/0200009 A1  Sep. 7, 2006

Related U.S. Application Data

(60) Provisional application No. 60/657,913, filed on Mar. 2, 2005.

(51) Int. Cl.
*A61B 5/00* (2006.01)
*G06F 19/00* (2011.01)

(52) U.S. Cl.
CPC ................................. *G06F 19/30* (2013.01)
USPC .............................................. 600/301; 705/2

(58) Field of Classification Search
USPC .................. 600/300–301; 128/903, 904, 920; 340/539, 573.1; 705/2–4
See application file for complete search history.

(56) References Cited

U.S. PATENT DOCUMENTS

| | | | |
|---|---|---|---|
| 3,618,592 A | 11/1971 | Stewart | |
| 4,513,294 A | 4/1985 | Anderson et al. | |
| 4,697,450 A | 10/1987 | Bachman et al. | |
| 4,869,253 A | 9/1989 | Craig, Jr. et al. | |
| 4,944,305 A | 7/1990 | Takatsu | |
| 5,197,480 A | 3/1993 | Gebhardt | |
| 5,262,944 A | 11/1993 | Weisner et al. | |
| 5,339,826 A | 8/1994 | Schmidt et al. | |
| 5,419,332 A | 5/1995 | Sabbah et al. | |
| 5,438,983 A | 8/1995 | Falcone | |
| 5,584,291 A | 12/1996 | Vapola et al. | |
| 5,718,235 A | 2/1998 | Golosarsky et al. | |
| 5,724,025 A * | 3/1998 | Tavori | 600/300 |
| 5,749,367 A | 5/1998 | Gamlyn et al. | |
| 5,800,360 A | 9/1998 | Kisner et al. | |
| 6,063,028 A | 5/2000 | Luciano | |

(Continued)

FOREIGN PATENT DOCUMENTS

| | | |
|---|---|---|
| EP | 1054338 | 11/2000 |
| GB | 2389290 | 12/2003 |

(Continued)

OTHER PUBLICATIONS

Supplementary European Search Report, Nov. 25, 2009, Spacelabs Medical/PCT/US2006/007269.

(Continued)

*Primary Examiner* — Bill Thomson
*Assistant Examiner* — Bobby Soriano
(74) *Attorney, Agent, or Firm* — Novel IP

(57) ABSTRACT

The present invention is a novel method of generating and representing the status of various physiological parameters that are monitored for patients during hospitalization. The system of present invention allows healthcare providers to easily view, at a glance, the status of a plurality of patients as well as any changes in the parameter values.

6 Claims, 13 Drawing Sheets

(56) References Cited

U.S. PATENT DOCUMENTS

| | | |
|---|---|---|
| 6,134,537 A | 10/2000 | Pao et al. |
| 6,322,502 B1 | 11/2001 | Schoenberg et al. |
| 6,347,310 B1 | 2/2002 | Passera |
| 6,383,136 B1 | 5/2002 | Jordan |
| 6,443,889 B1 | 9/2002 | Groth et al. |
| 6,571,227 B1 | 5/2003 | Agrafiotis et al. |
| 6,647,341 B1 | 11/2003 | Golub et al. |
| 6,650,779 B2 | 11/2003 | Vachtesvanos et al. |
| 6,702,754 B2 | 3/2004 | Ogura et al. |
| 6,771,172 B1 | 8/2004 | Robinson et al. |
| 6,804,656 B1 | 10/2004 | Rosenfeld et al. |
| 7,031,857 B2 | 4/2006 | Tarassenko et al. |
| 7,081,091 B2 * | 7/2006 | Merrett et al. ............ 600/300 |
| 7,256,708 B2 | 8/2007 | Rosenfeld et al. |
| 7,315,825 B2 | 1/2008 | Rosenfeld et al. |
| 7,371,214 B2 * | 5/2008 | Kouchi et al. ............ 600/300 |
| 2003/0117296 A1 | 6/2003 | Seely |
| 2004/0032426 A1 | 2/2004 | Rutledge et al. |
| 2004/0054261 A1 * | 3/2004 | Kamataki et al. ............ 600/300 |
| 2004/0103001 A1 | 5/2004 | Mazar |
| 2004/0153257 A1 | 8/2004 | Munk |

FOREIGN PATENT DOCUMENTS

| | | |
|---|---|---|
| GB | 2389290 | 11/2005 |
| JP | 07-163527 | 6/1995 |
| JP | 2003210422 | 7/2003 |
| WO | WO 03/091841 | 11/2003 |
| WO | WO 03/102850 | 12/2003 |

OTHER PUBLICATIONS

Schoenberg, Roy, MD; Sands, Daniel Z., MD MPH; Safran, Charles, MD; Center for Clinical Computing, Beth Israel Deaconess Medical Center, Harvard Medical School, "Making ICU Alarms Meaningful: a comparison of traditional vs. trend-based algorithms" (AMIA '99 Annual Symposium), 1999, pp. 1-5.

Report on Patentability, PCT/US2006/007269, Aug. 26, 2009, Spacelabs Medical.

* cited by examiner

TRENDING DISPLAY OF PATIENT WELLNESS

CROSS-REFERENCE TO RELATED APPLICATIONS

The present invention relies on, for priority, U.S. Provisional Application No. 60/657,913, entitled "Continuous Trending Display of Parameter Status", filed on Mar. 2, 2005.

FIELD OF THE INVENTION

The present invention relates generally to the field of medical systems for monitoring physiological parameters of patients and, more particularly, to improved methods and apparatuses for displaying information related to such monitored physiological parameters. More specifically, the present invention relates to improved methods and apparatuses for retrospectively and prospectively displaying patient wellness, both by individual parameter trending and by calculating an overall wellness indicator.

BACKGROUND OF THE INVENTION

Patient monitoring systems are commonly used in hospitals, such as in intensive care units (ICUs), for monitoring patient status and condition. Conventional patient monitoring systems typically include a bedside monitor having one or more sensors attached to the patient, for sensing parameters such as ECG, blood pressure, blood oxygen, blood glucose and temperature. The output from the sensors is sent to a system processor, which subsequently processes the measured values. These values may then be displayed on a video display screen or stored for later analysis. Data representing the measured physiological parameters is typically displayed as waveforms and/or numerical values.

Conventional patient monitoring systems are also capable of handling critical patient events or alarm conditions. For example, when the value of one of the physiological parameters being monitored exceeds a predetermined threshold value and/or meets predetermined alarm criteria, an alarm is activated by the bedside monitor and subsequently transmitted to a central monitoring station. The alarm can be annunciated at the central station in various ways, such as by highlighting relevant parameter information. An audible alarm is also typically generated at the central station.

In any information intensive or demanding medical environment, such as an intensive care unit, it is important to present the information on the display screen of a patient monitoring system in a clear and unambiguous manner. However, conventional patient monitoring systems are limited in their ability to present a comparison or evaluation of changing patient diagnostic variables. Although the conventional systems are useful in accumulating much useful data, accessing the data is oftentimes difficult and time-consuming.

Several patient monitoring systems have been disclosed in the prior art as highlighting critical patient events and alarm conditions. For example, U.S. Pat. No. 5,438,983, assigned to Koninklijke Philips Electronics, discloses "a patient monitoring system comprising: a sensor for measuring values representative of a physiological parameter; and a processor coupled to said sensor for processing said parameter values measured by said sensor, said processor comprising: means for determining whether said parameter values are within safe zone limits; means for initiating calculation of a trend vector when said parameter values go outside said safe zone limits, said trend vector being a function of changes in said parameter values and time; means for comparing said trend vector with an alarm limit function; and means for issuing an alarm when said trend vector exceeds said alarm limit function".

Prior art patient monitoring systems also include sensor systems that provide output signals indicative of normal, above normal or below normal sensed conditions. The signals may be used to monitor a condition and may be combined so that specific combinations of abnormal signals provide an indication of the condition of the patient. Although the prior art systems attempt to simultaneously communicate large amounts of patient data and information, these systems are lacking in that they do not provide the physician or clinician with efficient and effective means for quickly analyzing data in an information-rich environment.

In addition, with current patient monitoring systems, individual health parameters are typically seen as individual data elements. Clinicians look at each parameter separately to assess the composite trends of the status of the patient. Thus, it is often a time-consuming challenge for health care providers to accurately assess multiple parameters in context, thus resulting in errors or missed data, and further resulting in poor decisions regarding patient status.

What is therefore needed are methods, systems and apparatuses for monitoring of patient physiological parameters that facilitate in the assessment of patient status and patient health on a unified display.

What is also needed is a patient monitoring device that is able to continuously present the status of at least one measured parameter in a clear and concise manner, thus aiding healthcare providers in making decisions and drawing conclusions on patient wellness despite being confronted by substantial amounts of information in stressful environments such as an intensive care unit.

What is also needed is a patient monitoring device for recognizing data from a plurality of parameters indicating patient wellness status in a unified display.

What is also needed is a patient monitoring device that is able to continuously present the status of a plurality of measured parameters in a clear and concise manner, thus aiding healthcare providers in making decisions and drawing conclusions on patient wellness.

Furthermore, what is needed is a patient monitoring system in which alarm conditions are clearly presented on the display screen of the patient monitoring system, such that a life-threatening patient condition can be differentiated from other, less serious alarms or with alarms that have already been acknowledged.

SUMMARY OF THE INVENTION

The present invention is a medical system for monitoring physiological parameters of patients and, more specifically, an improved method and apparatus for monitoring of patient physiological parameters that facilitate in the assessment of patient status and wellness and for displaying information related to patient status and wellness.

Still more specifically, the present invention is an improved method and apparatus for displaying patient wellness status, both by individual parameter trending and by calculating an overall wellness indicator.

In one embodiment, the present invention is a method of generating and representing the status of at least one physiological parameter of a patient and displaying the status on the display portion of a medical system for monitoring physiological parameters of a patient.

In one embodiment, the present invention is a method of generating, representing, and calculating the status of a plurality of physiological parameters of a patient and displaying the status on the display portion of a medical system for monitoring physiological parameters of a patient.

In another embodiment, the present invention is a patient monitoring system in which a clinician is provided a defined rules-based view that will assist in accurate assessment of multiple parameters in a unified context and further, the overall wellness status of the patient.

The patient monitoring system of the present invention continuously presents the status of measured physiological parameters in a clear and concise manner. Thus, the present invention is, in one embodiment, a patient monitoring system in which patient status with respect to overall wellness or individual parameter wellness are clearly presented on the display screen of the patient monitoring system, such that a life-threatening patient condition can be differentiated from other, less serious alarms or with alarms that have already been acknowledged.

In one embodiment, the overall wellness status of the patient represents an indication of a calculated composite of multiple physiological parameters.

In one embodiment, the system of the present invention enables healthcare providers to view, at a glance, the overall wellness status of at least one of a plurality of patients.

In one embodiment of the present invention, the system comprises both a visual retrospective and visual prospective trending display that provides a summary of a patient's overall wellness status within a predefined time period by combining the values of a user-defined group of data elements, including but not limited to physiological parameters, weight, age, and other calculations according to a rules-based engine algorithm. The user can thus configure the rules of the visual trending display by changing the individual parameters hard ceiling values, slope, timing, and calculations.

In one embodiment, the wellness status of a patient is represented on a display as a horizontal trend bar.

In one embodiment, the system of the present invention enables healthcare providers to view, at a glance, individual parameter wellness status of at least one patient. Optionally, the healthcare provider is able to view any changes in the individual parameter values.

In one embodiment, the individual parameter wellness status of the patient represents an indication of changes of at least one individual parameter value for a particular patient. In one embodiment, the indication of changes of at least one individual parameter value is based upon pre-determined threshold values.

In one embodiment, the individual parameter wellness status of a patient is represented on a display as a vertical trend bar. In one embodiment, the present invention comprises applying a distinctive color or shape to a portion of an individual patient parameter zone representing the status of an individual parameter. For example, with vertically-displayed parameter zones, the colored and/or shaped areas of the parameter zone visually comprise a vertical color light bar in one construction.

In one embodiment, the trend bar employs multiple colors and blends of multiple colors, such as but not limited to green, yellow and red to indicate levels and changes in the patient's retrospective status and allow composite views of the data over time.

In one embodiment, the present invention further comprises a predictive indicator. Preferably, the predictive indicator is an icon that displays a color indicator of the prospective trend for the future based upon configurable predictive rules. The color of the indicator is chosen as one that is distinct, such as, but not limited to green, yellow, and red. The trending indicators themselves are thus embodied in both hardware and/or software implementations.

In one embodiment, the trend bar is always visible; thus, a clinician can easily view simple trending information at a glance. The trend bar also serves as a "hot-link" to further display the data in more detail, including a miniature parameter trend display. The light bar trending is preferably user-defined for the density of the trend information as well as the duration of the data included. A corresponding rules-based engine takes into consideration user-defined upper and lower limits, baseline, slope, time, and calculations.

In one embodiment, the present invention is a system for monitoring a physiological condition of an individual, comprising: at least one sensor for measuring at least one physiological parameter and providing data on said physiological parameter; a display unit coupled to the at least one sensor and configured for displaying in real-time the physiological parameter data provided by said sensor unit; and an inference engine coupled to said display unit and the at least one sensor for combining a plurality of said physiological parameter data to generate an indicator of the individual's general health, not limited to a single physiological parameter, and transmit said indicator to the display unit.

Optionally, the system further comprises a central monitoring unit remote from said display unit and adapted for receiving said indicator of the individual's general health and physiological parameter data from said display unit.

In one embodiment, the measured physiological parameters comprise at least one of pulse rate, ECG, blood oxygen saturation level ($SpO_2$), respiratory rate, blood glucose level, blood pressure and body temperature. In one embodiment, the physiological parameters are visually represented by a plurality of colors and shapes, which appear as light bars. Optionally, the light bars can act as a link to detailed parameter trending information, including an electronic patient record.

In another embodiment, the present invention is a method for monitoring the physiological condition of an individual comprising the steps of: measuring at least one physiological parameter with a sensor unit; providing data on said physiological parameter; displaying in real-time the physiological parameter data provided by the sensor on a display unit; combining a plurality of said physiological parameter data to generate an indicator of the individual's general health, not limited to a single parameter; and transmitting said indicator to the display unit. Optionally, the method of the present invention may further comprise the step of receiving said indicator of the individual's general health and physiological parameter data from said display unit at a central monitoring station. In one embodiment, the step of combining a plurality of said physiological parameter data to generate an indicator of the individual's general health, is achieved via an inference engine. In one embodiment, the inference engine operates using rules and said rules are based on custom defined factors including upper and lower limits of physiological parameters, baseline of physiological parameters, slope, time and calculations.

In yet another embodiment, the present invention is a system for monitoring the physiological condition of an individual, comprising: at least one sensor for measuring at least one physiological parameter and providing data on said physiological parameter; a display unit coupled to the at least one sensor and configured for displaying in real-time the physiological parameter data provided by said sensor unit; an inference engine coupled to said display unit and the at least one sensor for combining a plurality of said physiological parameter data to generate an indicator of the individual's future health, not limited to a single physiological parameter, and transmit said indicator to the display unit; and a central monitoring unit remote from said display unit and adapted for receiving said indicator of the individual's future health and physiological parameter data from said display unit.

In yet another embodiment, the present invention is a system for monitoring a physiological condition of an individual, comprising: at least one sensor for measuring at least one physiological parameter and providing data on said physiological parameter; a display unit coupled to the at least one sensor and configured for displaying in real-time the physiological parameter data provided by said sensor unit; an inference engine coupled to said display unit and the at least one sensor for combining a plurality of said physiological parameter data to generate an indicator of the individual's general health, not limited to a single physiological parameter, and transmit said indicator to the display unit; and a central monitoring unit remote from said display unit and adapted for receiving said indicator of the individual's general health and physiological parameter data from said display unit; and wherein said display unit and said central monitoring unit are configured to display parameter data using colors and shapes representing the status of parameters, and wherein said colors and shapes are always visible.

In another embodiment, the present invention is a method for monitoring the physiological condition of an individual comprising the steps of: measuring at least one physiological parameter with a sensor unit; providing data on said physiological parameter; displaying in real-time the physiological parameter data provided by the sensor on a display unit; combining a plurality of said physiological parameter data to generate an indicator of the individual's general health, not limited to a single parameter; transmitting said indicator to the display unit; and receiving said indicator of the individual's general health and physiological parameter data from said display unit at a central monitoring station; and wherein parameter data is displayed using colors and shapes representing the status of parameters, and wherein said colors and shapes are always visible.

In yet another embodiment, the present invention is a system for monitoring a physiological condition of an individual, comprising: at least one sensor for measuring at least one physiological parameter and providing data on said physiological parameter; a display unit coupled to the at least one sensor and configured for displaying in real-time the physiological parameter data provided by said sensor unit; an inference engine coupled to said display unit and the at least one sensor for combining a plurality of said physiological parameter data to generate an indicator of the individual's general health, not limited to a single physiological parameter, and transmit said indicator to the display unit; and a central monitoring unit remote from said display unit and adapted for receiving said indicator of the individual's general health and physiological parameter data from said display unit; wherein said display unit and said central monitoring unit are configured to display overall individual status using a trend bar representing the combined status of parameters and an icon representing a prediction of the future combined status of parameters.

In yet another embodiment, the present invention is a system for monitoring a physiological condition of an individual, comprising: at least one sensor for measuring at least one physiological parameter and providing data on said physiological parameter; a display unit coupled to the at least one sensor and configured for displaying in real-time the physiological parameter data provided by said sensor unit; and an inference engine coupled to said display unit and the at least one sensor for combining a plurality of said physiological parameter data to generate an indicator of the individual's general health, not limited to a single physiological parameter, and transmit said indicator to the display unit; and a central monitoring unit remote from said display unit and adapted for receiving said indicator of the individual's general health and physiological parameter data from said display unit.

In yet another embodiment, the present invention is a method for monitoring the physiological condition of an individual comprising the steps of: measuring at least one physiological parameter with a sensor unit; providing data on said physiological parameter; displaying in real-time the physiological parameter data provided by the sensor on a display unit; combining a plurality of said physiological parameter data to generate an indicator of the individual's general health, not limited to a single parameter; transmitting said indicator to the display unit; and receiving said indicator of the individual's general health and physiological parameter data from said display unit at a central monitoring station.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following Detailed Description when considered in connection with the accompanying drawings, wherein.

DETAILED DESCRIPTION OF THE INVENTION

Figure 1:
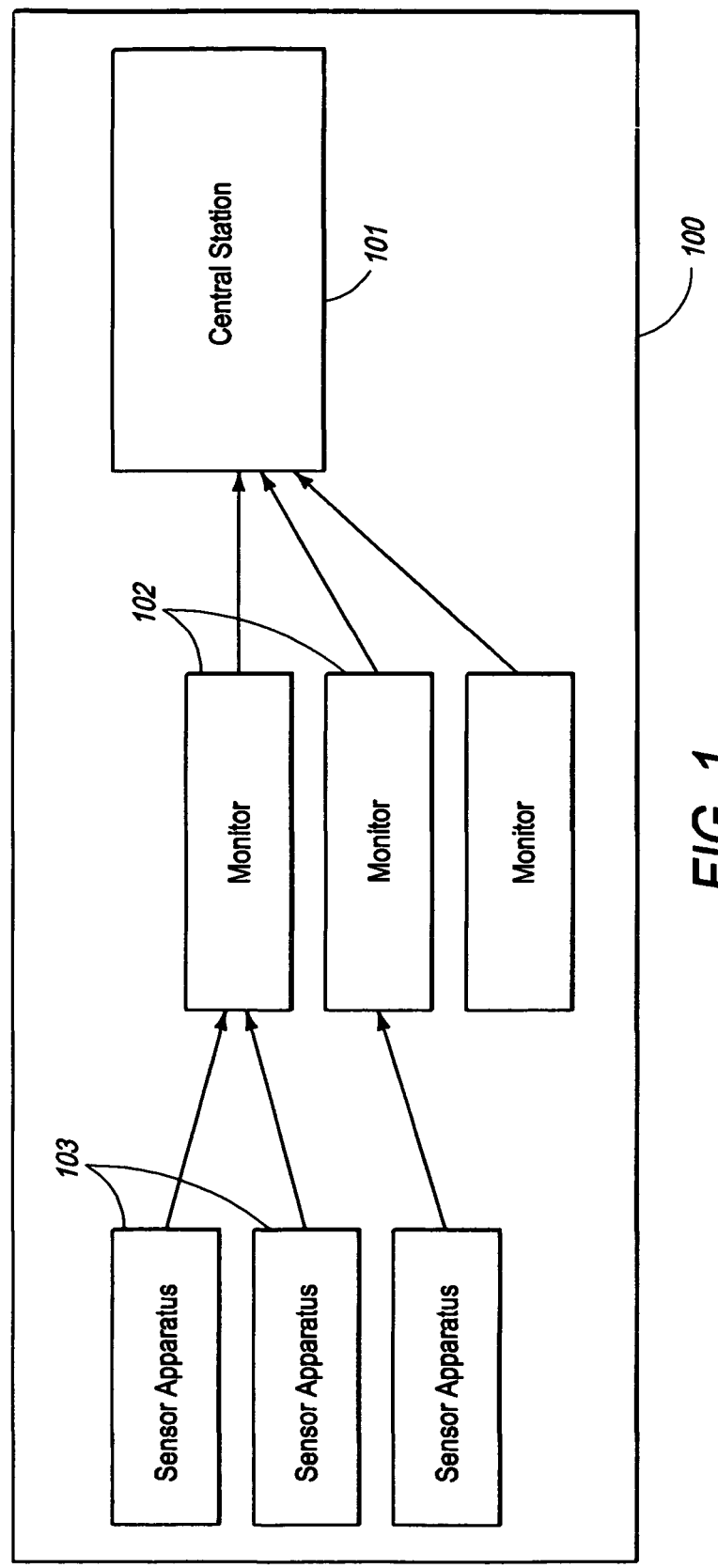
FIG. 1 is a diagrammatic illustration of one embodiment of a patient monitoring apparatus as used in the present invention.

The present invention is directed towards medical systems for monitoring physiological parameters of patients and, more particularly, to improved methods and apparatuses for displaying information related to monitored physiological parameters.

More specifically, the present invention is directed towards methods, systems and apparatuses for monitoring of patient physiological parameters that facilitate in the assessment of patient status and wellness.

Still more specifically, the present invention is directed towards improved methods and apparatuses for displaying patient wellness status, both by individual parameter trending and by calculating an overall wellness indicator.

In addition, the present invention is directed towards a method of generating and representing the status of at least one physiological parameter of a patient and displaying the status on the display portion of a medical system for monitoring physiological parameters of a patient.

In addition, the present invention is directed towards a method of generating, representing, and calculating the status of a plurality of physiological parameters of a patient and displaying the status on the display portion of a medical system for monitoring physiological parameters of a patient.

In addition, the present invention is directed towards a patient monitoring system in which a clinician is provided a defined rules-based view that will assist in accurate assessment of multiple parameters in a unified context and further, the overall wellness status of the patient.

In addition, the patient monitoring system of the present invention is able to continuously present the status of measured physiological parameters in a clear and concise manner. Thus, the present invention is also directed towards a patient monitoring system in which patient status with respect to overall wellness or individual parameter wellness are clearly presented on the display screen of the patient monitoring system, such that a life-threatening patient condition can be differentiated from other, less serious alarms or with alarms that have already been acknowledged.

In one embodiment, the overall wellness status of the patient represents an indication of a calculated composite of multiple physiological parameters.

In one embodiment, the system of the present invention enables healthcare providers to view, at a glance, the overall wellness status of at least one of a plurality of patients.

In one embodiment of the present invention, the system comprises both a visual retrospective and visual prospective trending display that provides a summary of a patient's overall wellness status within a predefined time period by combining the values of a user-defined group of data elements, including but not limited to physiological parameters, weight, age, and other calculations according to a rules-based engine algorithm. The user can thus configure the rules of the visual trending display by changing the individual parameters hard ceiling values, slope, timing, and calculations.

In one embodiment, the wellness status of a patient is represented on a display as a horizontal trend bar.

In one embodiment, the system of the present invention enables healthcare providers to view, at a glance, individual parameter wellness status of at least one patient. Optionally, the healthcare provider is able to view any changes in the individual parameter values.

In one embodiment, the individual parameter wellness status of the patient represents an indication of changes of at least one individual parameter value for a particular patient. In one embodiment, the indication of changes of at least one individual parameter value is based upon pre-determined threshold values.

In one embodiment, the individual parameter wellness status of a patient is represented on a display as a vertical trend bar. In one embodiment, the present invention comprises applying a distinctive color or shape to a portion of an individual patient parameter zone representing the status of an individual parameter. For example, with vertically-displayed parameter zones, the colored and/or shaped areas of the parameter zone visually comprise a vertical color light bar in one construction.

In one embodiment, the trend bar employs multiple colors and blends of multiple colors, such as but not limited to green, yellow and red to indicate levels and changes in the patient's retrospective status and allow composite views of the data over time.

In one embodiment, the present invention further comprises a predictive indicator. Preferably, the predictive indicator is an icon that displays a color indicator of the prospective trend for the future based upon configurable predictive rules. The color of the indicator is chosen as one that is distinct, such as, but not limited to green, yellow, and red. The trending indicators themselves are thus embodied in both hardware and/or software implementations.

In one embodiment, the trend bar is always visible; thus, a clinician can easily view simple trending information at a glance. The trend bar also serves as a "hot-link" to further display the data in more detail, including a miniature parameter trend display. The light bar trending is preferably user-defined for the density of the trend information as well as the duration of the data included. A corresponding rules-based engine takes into consideration user-defined upper and lower limits, baseline, slope, time, and calculations.

Various modifications to the preferred embodiment will be readily apparent to those of ordinary skill in the art, and the disclosure set forth herein may be applicable to other embodiments and applications without departing from the spirit and scope of the present invention and the claims appended hereto. Thus, the present invention is not intended to be limited to the embodiments described, but is to be accorded the broadest scope consistent with the disclosure set forth herein.

FIG. 1 is a diagrammatic illustration of one embodiment of a patient monitoring apparatus as used in the present invention. Referring now to FIG. 1, in one embodiment of the present invention, patient monitoring system 100 comprises central monitoring station 101 and at least one monitor 102, which is preferably located at a patient bedside. In one embodiment, central station 101 is located at a nursing station or similar centrally located hospital staff location. As described in greater detail below, selected patient information received at central station 101 from at least one monitor 102 is presented on a video display (not shown) attached to the central station.

In one embodiment, each monitor 102 communicates with sensor apparatus 103, which further comprises at least one sensor (not shown). The sensor is attached to the patient (not shown) and is used to record various physiological parameters of the patient, such as but not limited to heart rate, ECG, invasive blood pressure, non-invasive blood pressure, body temperature (oral, rectal, and tympanic), respiration, entidal carbon dioxide, oxygen, cardiac output, $SPO_2$, $SVO_2$, and various anesthesia gases.

In one embodiment, the individual obtains a measurement of at least one physiological parameter and translates these values into analog signals. The signals are then digitized. Bedside monitor 102 thus records physiological information obtained from the sensor apparatus 103 and transmits the patient information to central station 101.

One of ordinary skill in the art would appreciate that communication between the sensor apparatus and the monitor and between monitors and the central station may take place using any suitable wired or wireless medium and include communications based on Bluetooth, Ethernet, 802.11(x) standards, or any other wireless protocol.

Besides the measured parameter values, patient information may include any and all information contained in the patient's record, including but not limited to demographic information such as the patient's name, bed number, and the patient's identification (ID) number or the ID of the physician in charge of that patient. Optionally, the patient information can include height, weight, family medical history, X-ray information, laboratory results, and insurance information. As described in further detail below, monitors 102 typically comprise a display screen for displaying individual patient information.

In one embodiment of the present invention, the system comprises both a visual retrospective and visual prospective trending display that provides a summary of a patient's overall wellness status within a predefined time period by combining the values of a user-defined group of data elements, including but not limited to physiological parameters, weight, age, and other calculations according to a rules-based engine algorithm. For example, but not limited to such example, patient wellness may in part be calculated based upon the age of the patient and the corresponding heart rate coefficient at that particular age for a more accurate assessment. The user can thus configure the rules of the visual trending display by changing the individual parameters hard ceiling values, slope, timing, and calculations. In another embodiment of the present invention, the system comprises a visual display that provides a summary of a measured individual physiological parameter during a pre-determined time period.

Figure 2:
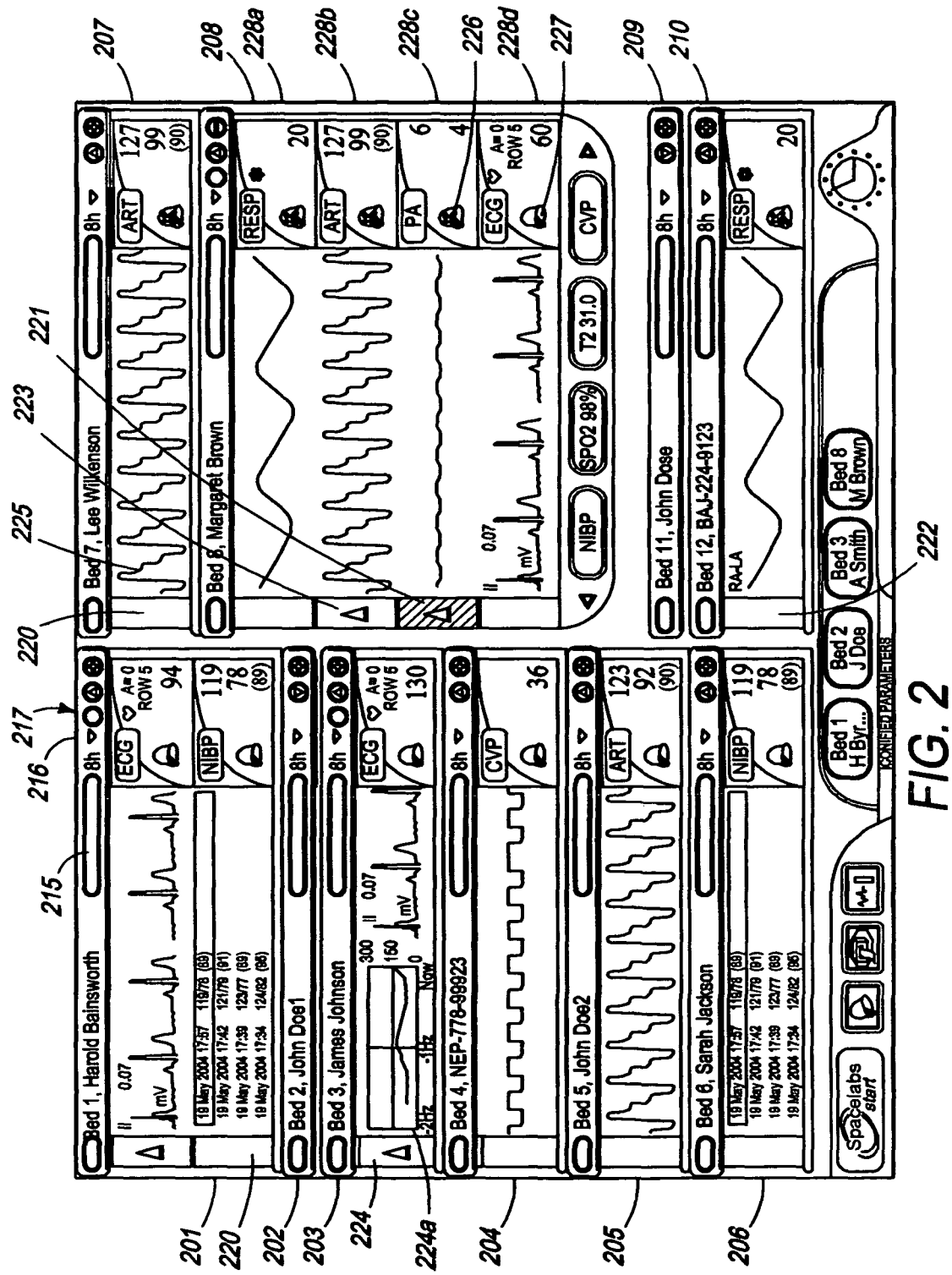
FIG. 2 is an illustration of one embodiment of a central station patient information display of the present invention.

FIG. 2 is an illustration of one embodiment of a central station patient information display of the present invention, illustrating both an overall patient wellness status trend bar and an individual parameter patient wellness status trend light bar.

In one embodiment, the central station display is divided into a plurality of sections 201, 202, 203, 204, 205, 206, 207, 208, 209, and 210. Section 201, 202, 203, 204, 205, 206, 207, 208, 209, and 210 preferably represent individual patient sections 201 210 201, 202, 203, 204, 205, 206, 207, 208, 209, and 210 and are employed to display physiological data for each patient, along with corresponding waveform, alarm, and patient demographic information. In one embodiment, to allow for better patient status recognition, the spatial arrangement of individual patient sections 201, 202, 203, 204, 205, 206, 207, 208, 209, and 210 corresponds with the actual physical arrangement of the respective patient monitors and/or beds. For example, but not limited to such example, individual patient section 208 corresponds to the bedside monitor for the patient in Bed 8, and displays information pertaining to a plurality of physiological parameters for the patient in Bed 8, including, but not limited to ECG, SPO$_2$, and CVP.

In one embodiment, the central station display further comprises a trending display. In one embodiment, the trending display is a continuous summary of at least one measured physiological parameter of a patient. In one embodiment, the trending display is a multiple parameter overall patient wellness bar. In one embodiment, the multiple parameter overall patient wellness bar is horizontal light bar 215. In another embodiment, the trending display is an individual parameter trend bar. In one embodiment, individual parameter trend bar is a vertical light bar 220, which is described in further detail below.

In one embodiment, the trend display bars 215 and 220 employ color or the intensity of light to represent a user-defined time period. In one embodiment, the user-defined time period is displayed proximate to trend bar 215, such as time period drop-down interval menu and indicator 216 adjacent to light bar 215. The time period may be dynamically altered or adjusted by accessing the time function in interval menu and indicator 216.

In one embodiment, a plurality of colors and/or shading variations are used to differentiate the summary information presented on the trend bar. For example, in one embodiment, the trend bar is shaded the color "green" to indicate a normal or "good" condition as indicated by a calculated composite on multiple physiological parameters. In another embodiment, the trend bar may be shaded yellow to indicate an alert condition, further indicating that the calculated composite of multiple physiological parameters has entered a borderline or warning stage and are close to exceeding a pre-defined threshold value or range of values. In another example, the trend bar may be shaded red to indicate a high alert condition, further indicating that one or more elements within the physiological parameter has exceeded a pre-defined threshold value or range of values.

Optionally, the width of a wellness bar may be divided into several viewable sections with each section representing a division of the trends during a selected time frame. Each section of the "bar" may optionally be displayed in the color representative of a calculated patient overall wellness during that portion of the selected time frame.

For example, referring back to FIG. 2, for a selected patient title bar, if a patient is monitored in an 8 hour interval, the light bar represents iterations of the 8 hour time interval as different colors, indicating a different overall patient status for each section of time in the 8 hour time interval bar. As shown in FIG. 2, wellness bar 215, configured to monitor in 8 hour intervals, illustrates a recent alert where the wellness bar section has turned from a green "good" status to a yellow "alert" status, which corresponds to the patient's overall wellness.

In one embodiment, the patient monitoring system of the present invention further comprises an inference engine. In one embodiment, the inference engine is an application that is capable of running on any system host. Preferably, the inference engine is employed to determine the status of various parameters and to enable the display of trend bars and trend waveforms. One of ordinary skill in the art would appreciate that the inference engine can be installed on any computing device and be compatible with any operating system, including Linux-based, Unix-based, Java-based or Microsoft-based operating systems. The inference engine is comprised of a plurality of rules and takes into consideration the upper and lower limits for different parameters, the baseline, slope, time and other calculations, as defined by prevailing standards or as clinician-defined.

Additionally, the rules-based engine allows the clinician to define individual parameter threshold values, including but not limited to slope, timing, duration of the display bar or icon, and the combination of composite calculated values. The user can thus assign threshold values that define the range of "normal", "alert", and "high alert", among others, depending on the measured parameter and individual patient status.

Optionally, clinicians may modify inference engine rules in accordance with individual patient conditions. For example, standard blood pressure limits are 80 millimeters diastolic and 120 millimeters systolic. For patients in an older age bracket or those with a history of high blood pressure, blood pressure limits may be set to slightly higher than the standard, such as 90 millimeters diastolic and 140 millimeters systolic, as deemed safe for an individual patient by his treating physician. Thus, the patient monitoring system of the present invention provides the physician with the ability to adapt the rules that determine the status of various body parameters to suit the specific requirements of individual patients.

In one embodiment, central station display further comprises a predictive display, which is preferably an icon, such as but not limited to icon 217. In one embodiment, icon 217 is an open/close icon for parameter display rules and trend data. In one embodiment, the predictive model display icon is positioned proximate to the trending bars and displays a color indicator of the prospective trend for future patient diagnostics based upon a configurable predictive rules engine. In one embodiment the predictive icons represent a user-defined time period and employs different colors to indicate the patient status at the pre-defined time period. Data is thus collected in user-defined time increments and is preferably hierarchical when the collected data displayed is at a maximum. More specifically, the newer collected data is displayed in preference to older data.

In one embodiment, when there is no data collected during a particular time period, the trend bar or predictive icon remains clear or not colored in. In another embodiment, the monitor displays a "blank" during a time period in which no data is collected. The display bar or icon progressively migrates through the visible display area sections as time passes.

As mentioned above, in another embodiment, the trending display is an individual parameter trend bar. In one embodiment, individual parameter trend bar is vertical color light bar 220, but is not limited to such embodiment. Optionally, individual parameter trend bar remains visible to staff positioned at the central monitoring station. Optionally, different colors are used to highlight the trend bar to indicate a change in parameter values. This enables the clinicians to view simple trending information and thus ascertain individual parameter patient wellness status at a glance.

Referring back to FIG. 2, a plurality of colors and/or shading variations are used to differentiate the information presented on the individual parameter trend bar. For example, in one embodiment, trend bar 220 is shaded the color "green" to indicate a normal or "good" condition, further indicating that the physiological parameter reading from the patient is within defined safe limits. In another embodiment, trend bar 220 is shaded yellow, indicating an alert condition, further indicating that one or more physiological parameter elements have entered a borderline or warning stage and is close to exceeding a pre-defined threshold value or range of values. In another example, trend bar 220 is shaded red and illustrates a high alert condition, further indicating that one or more elements within the physiological parameter has exceeded a pre-defined threshold value or range of values.

In addition, the trend bar may further comprise shading to represent a change in the status of the rules that are employed to define safe and alarm limits for the physiological parameter for a particular patient. More specifically, but not limited to such examples, a striped trend bar 221 is indicative that one or more rules for a particular physiological parameter in the rules-based engine is deactivated. In another example, but not limited to such example, a clear trend bar 222 (i.e. one that is not colored) indicates that trending for a particular parameter has been deactivated.

In addition, in one embodiment, a vertically positioned arrow 223 may be displayed within the individual parameter trend bar to indicate the direction of change of parameter values. For example, but not limited to such example, a drop in blood pressure is represented by a downward pointing arrow (↓) and a rise in blood pressure is represented by an upward pointing arrow (↑), as shown in FIG. 2.

In one embodiment, the individual parameter wellness bar is capable of providing a "hot-link" to provide further details about a particular parameter. In another embodiment, the overall patient wellness trend bar is capable of providing a "hot-link" to provide a wellness bar menu, which is described in further detail below. For example, but not limited to such example, clicking trend bar 224 results in the appearance of miniature parameter trend display 224a, as a graph or waveform in the parameter zone. Optionally, the trend bar may be used to act as an interrogation means for perusing the electronic patient record.

Although particular colors and shading trends are described with respect to this embodiment, it should be understood to those of ordinary skill in the art that any number of colors or variations of shading or stippling may be employed. The trend bar attributes for the various parameters with the help of light bars are user-defined, and thus can be set by the healthcare professionals who use the patient monitoring system. Such attributes include the density of trend information as well as the collection duration of data included.

In one embodiment, individual parameter trend bar 220, presents individual physiological parameter information in a plurality of visual forms. For example, but not limited to such example, trend bar 220 can represent the information contained within waveform 225. Optionally, trend bar 220 information can be presented in a variety of visual forms, including, but not limited to a numerical value.

In one embodiment, individual physiological parameter alarms are based upon pre-defined user threshold value or ranges of values. The alarm status is displayed as an icon 226 for "ALARM OFF" status or icon 227 for "ALARM ON" status. One of ordinary skill in the art should appreciate that any number of relevant physiological parameters can be configured and customized to either be displayed or hidden in the plurality of sections of the central station depending upon what physiological parameters are being monitored for a patient at the bedside and/or which of those are configured to be displayed at the central station display.

Optionally, each individual patient section is further arranged into zones, such as 228a, 228b, 228c, and 228d, corresponding to individual parameters. In addition, symbols of different colors and shapes are employed to reflect the overall status of at least one individual parameter.

Figure 3:
FIG. 3 is an illustration of another embodiment of a central station patient information display of the present invention.

FIG. 3 is an illustration of another embodiment of a central station patient information display of the present invention. In one embodiment, central station display is capable of providing an overall patient status wellness bar 301 for at least one patient. Optionally, the trending function of the multiple parameter wellness bar can be turned off and replaced by a numerical value. As shown in FIG. 3, wellness bar 305, configured to monitor at 8 hour intervals, has been turned off and is replaced by a numerical value of at least one physiological parameter measurement. The displayed individual parameter numerical value of the central station display can be set by the clinician or can optionally scroll through a plurality of parameters at pre-defined time intervals. For example, but not limited to such example, a clinician can optionally program the system to display the heart rate of a particular patient in the cardiology unit versus overall patient wellness.

FIGS. 4A, 4B, 4C and 4D are illustrations of the bedside monitor patient information display of the present invention, in which the wellness bar is activated. As described earlier the overall health state or "wellness" of a patient is a function of a plurality of user selected and defined physiological and/or demographic parameters that are interpreted and analyzed according to the configurable and user-defined rules in the rules-based engine.

In one embodiment, but not limited to such configuration the "wellness" of a patient is calculated as a function of one parameter, taking into consideration patient demographic. In another embodiment, the wellness of a patient is calculated as a function of a plurality of parameters. For example, but not limited to such example, the wellness of a patient is calculated using $SPO_2$ levels and ECG heart rate. More specifically, a calculation that incorporates the reduction in blood oxygen with a rising heart rate can be indicative of a serious problem, even though no individual parameter alarm has been triggered. The wellness parameter is thus calculated as a composite of at least one, and preferably a plurality of physiological parameters to indicate the overall health and wellness of a patient.

Figure 4A:
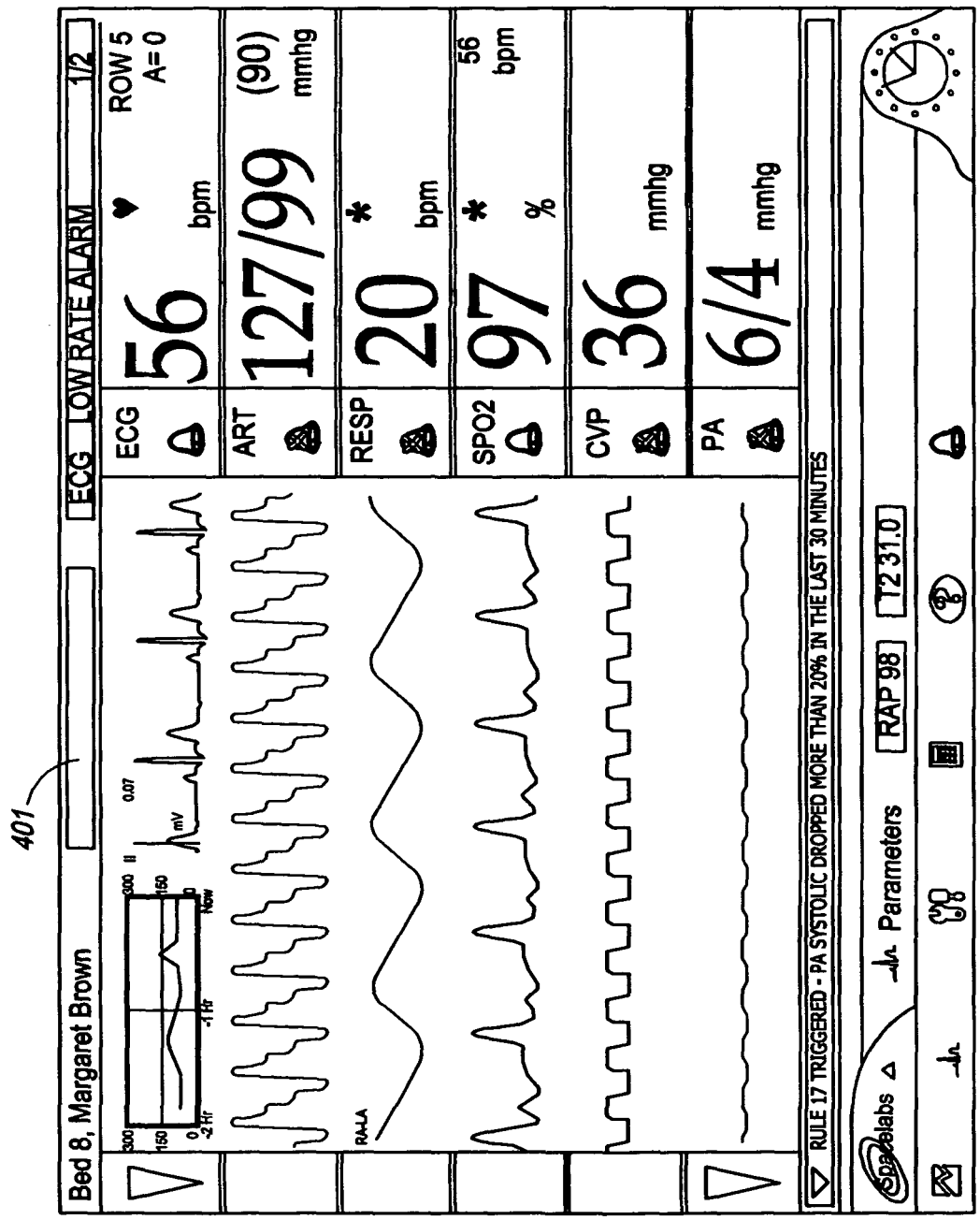
FIGS. 4A, 4B, 4C and 4D depict the bedside monitor patient information display of the present invention, in which the wellness bar is established.

FIG. 4A illustrates one embodiment of a patient bedside monitor 400 of the present invention in which the wellness bar is not activated. FIGS. 4A-4D are illustrations of the operational steps of activating the wellness bar. As shown in FIG. 4A, an operator can launch the wellness bar set-up screen (not shown) by touching wellness bar area 401.

Figure 4B:
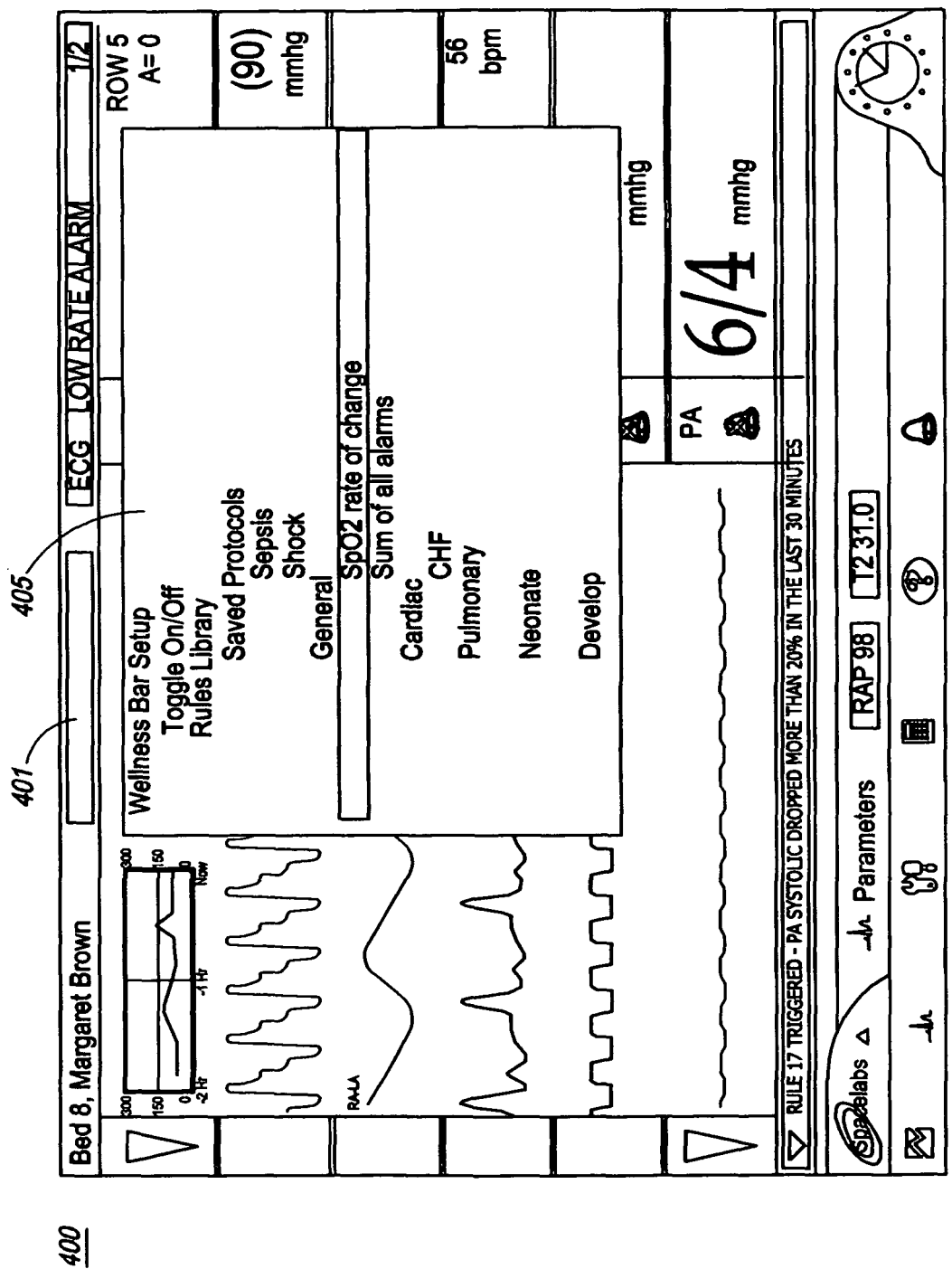
Figure 4C:
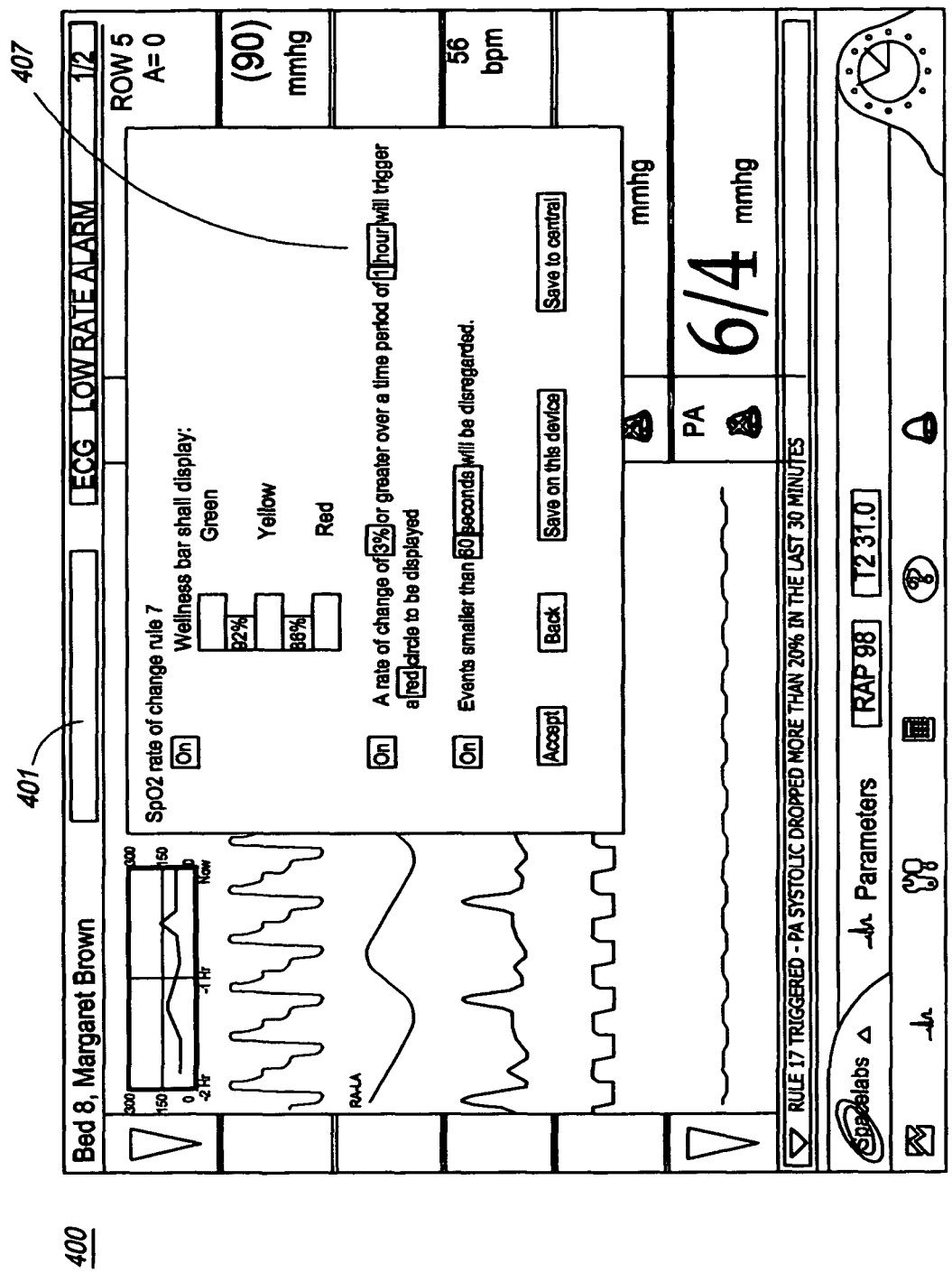

After touching wellness bar area 401, wellness bar set-up screen 405 is activated and shows the available templates and saved protocol libraries. As shown in FIG. 4B, the $SPO_2$ rate of change template is selected from wellness bar set-up screen 405. FIG. 4C depicts the $SPO_2$ rate of change template screen, which further depicts the $SPO_2$ rate of change rule. A plurality of manipulable options 407 are present on the rate of change rule screen, including but not limited to activating or deactivating the general rule, changing rule parameters, and accepting or negating the change of rule. The screen must be, accepted by the caregiver in order for the changes to take effect.

Figure 4D:
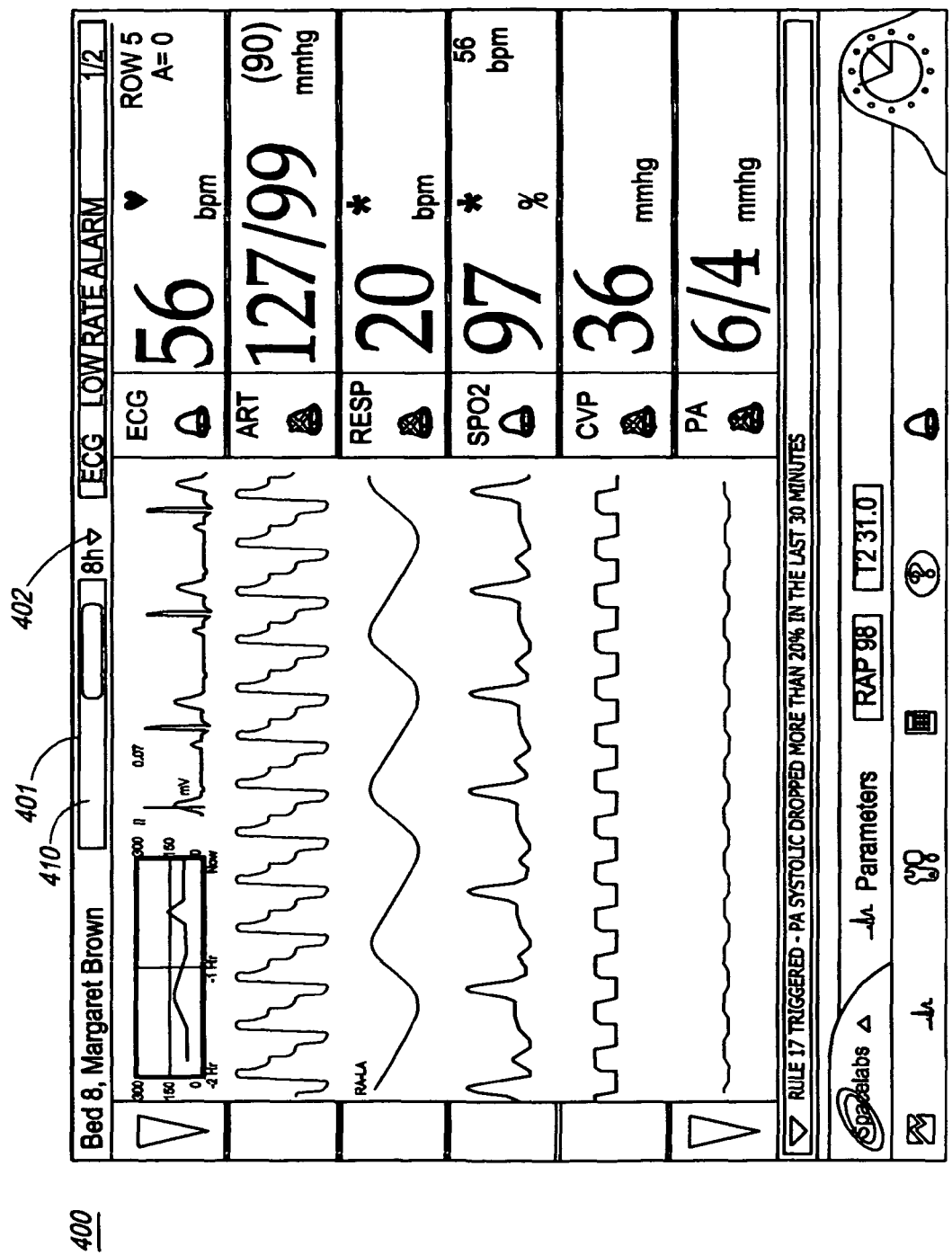

Once the changes are accepted, as shown in FIG. 4D, the wellness bar 410 is visible and active in wellness bar area 401. In one embodiment, integrated trend bar 401 is displayed as a yellow color which transitions to green which further transitions to yellow, covering the entire width of the trend bar. In one embodiment, the width of the trend bar correlates to an eight hour patient monitoring time interval, configured via time period interval drop down menu 402. Thus, in the example above, the patient's overall wellness, as represented by the colors in the integrated trend bar, has moved from an alert state to a normal state and back to an alert state in the span of eight hours.

The wellness bar can be touched to show the rules statement, toggle the wellness indicator on or off, and give access to the trending screens. Thus, as described above, the wellness bar serves as a "hot-link" to additional data.

Referring back to FIG. 4D, wellness bar 410 is correlated with the color displayed on the central station display described with respect to FIG. 2 above, and is indicative of overall patient condition for a plurality of measured physiological parameters. In addition, as described in further detail with respect to FIG. 11 below, when light bar 1100 on top of the bedside monitor is illuminated, a clinician is able to glance into the patient room and verify the patient's status. The colors displayed, as described above, are indicative of patient status.

Figure 5:
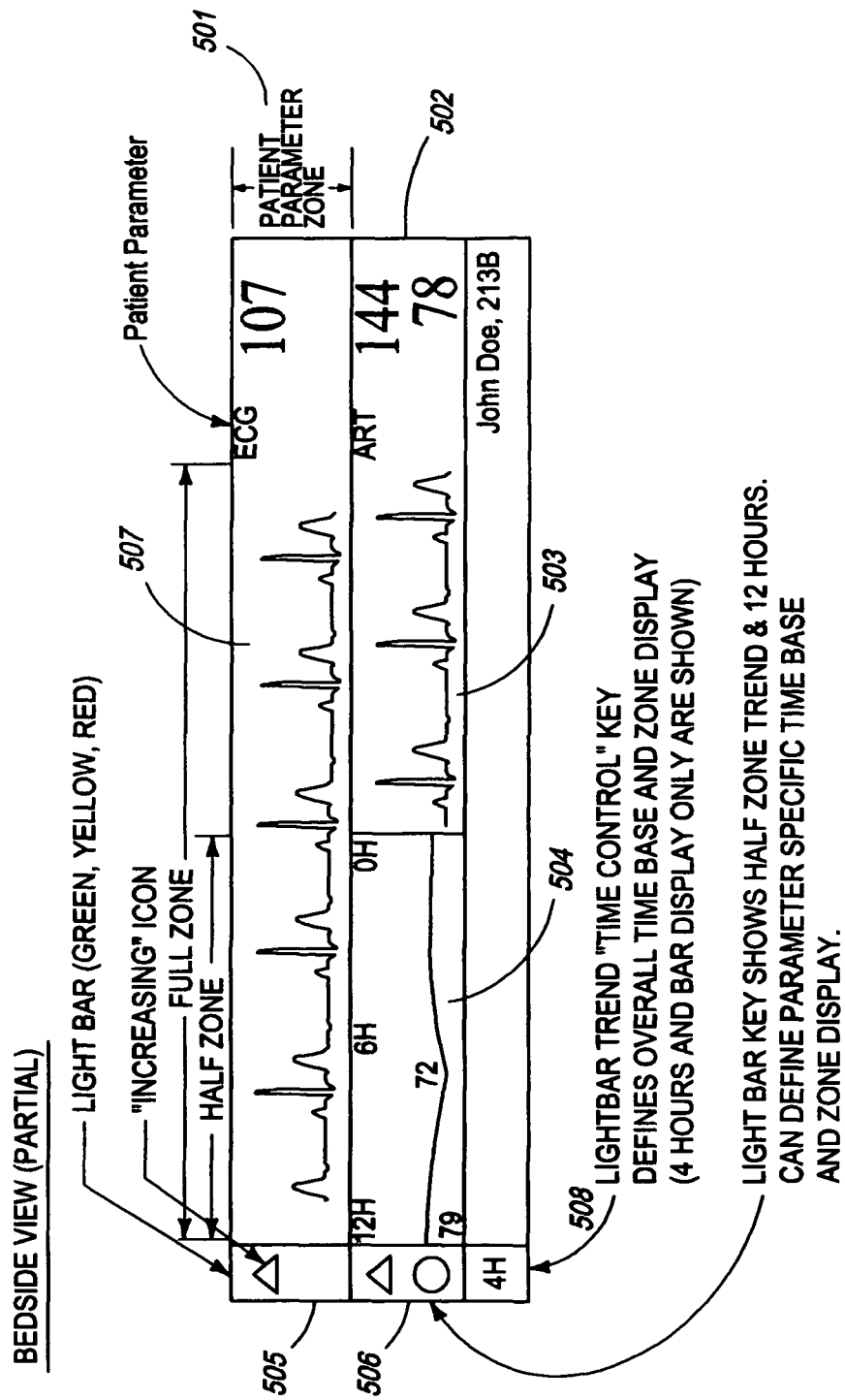
FIG. 5 depicts another embodiment of a bedside monitor patient information display of the present invention.

FIG. 5 illustrates one embodiment of a bedside monitor patient information display of the present invention, in a partial view. As described with respect to the central monitoring station display in FIG. 2, patient bedside monitor display is divided into zones, such as 501 and 502, each zone representing a specific patient parameter. In one embodiment, each parameter zone, such as zone 502, further comprises waveform area 503 reserved for displaying miniature trend graph 504 whenever required. In addition, parameter trend bars 505 and 506 are displayed adjacent to waveform areas 503 and 507, respectively, which are employed to exhibit, at a glance, whether a particular patient parameter is within a pre-defined threshold value or range of values, as defined by the user via the rules based inference engine.

Optionally, the time display range of miniature trend graph 504 can be individually configured for each parameter. Thus, the clinician can select a time range for which she wants to view physiological parameter data. Trend bar time control key 508 is provided on the controls of the bedside monitor for selecting the time range. In one embodiment, miniature trend graph 504 displays a default time range of twelve hours.

Optionally, trend graph 504 can be configured per parameter to be in a plurality of display states, including but not limited to displayed always, displayed at the clinician's request, or automatically displayed when a trend warning occurs, as determined by the rules of the inference engine.

The trend bar may optionally be configured by the healthcare personnel to track multiple elements or attributes per parameter. For example, ECG monitoring may comprise tracking a plurality of components such as, but not limited to heart rate, arrhythmia count, and ST. The trend bar may thus be configured to individually track the elements that comprise ECG monitoring and also provide a summation of the results.

Figure 6:
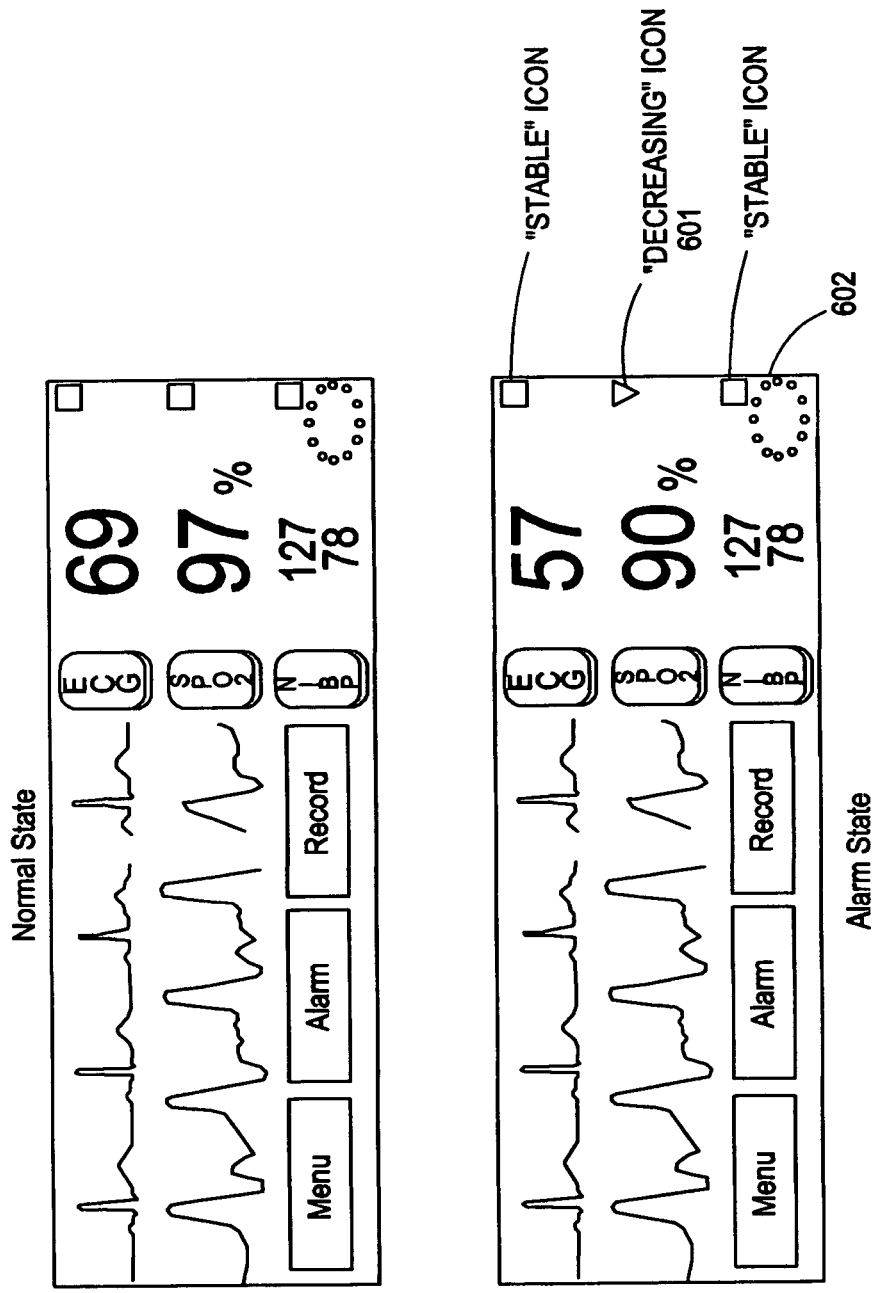
FIG. 6 is an illustration of one embodiment of a patient information display of the present invention.

FIG. 6 is an illustration of another embodiment of a patient information display of the present invention. More specifically, FIG. 6 represents a more simplified display of patient information in both a normal state and an alarm state. Different icons are used to represent the different states. As shown in FIG. 6, vertical arrow 601 is used to indicate a decrease (downward pointing arrow) in parameter value. In one embodiment, an upward vertical arrow may be used to indicate an increase in parameter value. Square block 602 is used to indicate a stable parameter status. Such visual indicators alert the healthcare provider or clinician with important information at a glance. For example, ECG data such as "20% change in ECG heart rate off baseline in last two hours, but still within the AHA approved alarm limits" can be discerned by a healthcare professional by simply looking at the display.

Figure 7:
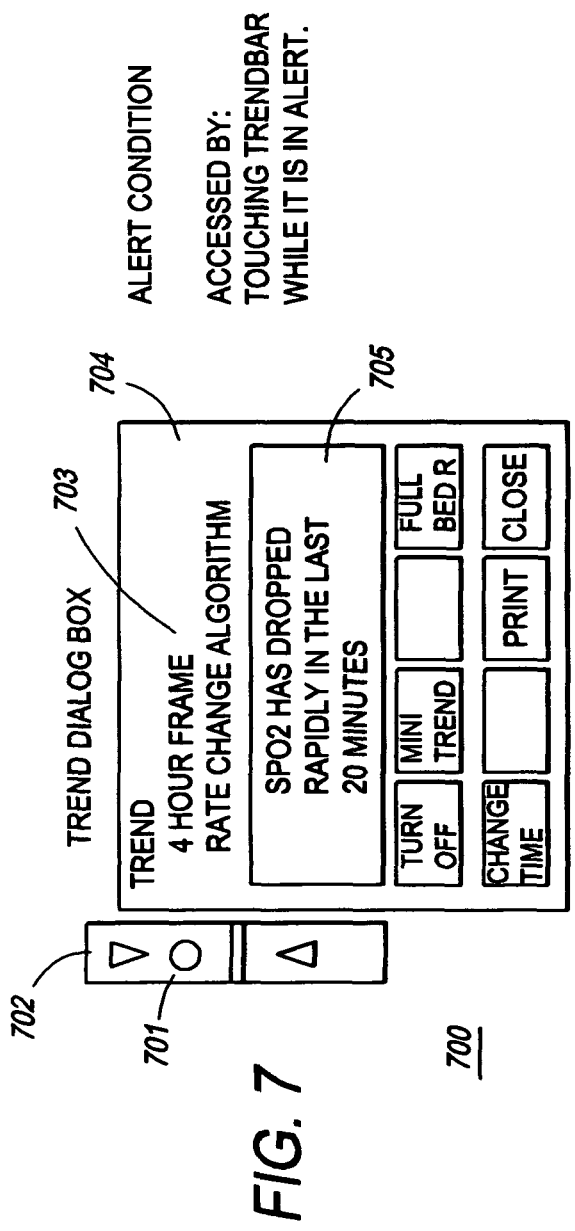
FIG. 7 depicts a trend display of the patient monitoring system of the present invention, further illustrating an alarm or alert condition.

FIG. 7 depicts a trend display of the patient monitoring system of the present invention, further illustrating an alarm or alert condition. In one embodiment, the nature of the alert condition is accessed by touching trend bar 701 while it is in an alert state. In one embodiment, the alert state is displayed by a trend alert arrow 702. In one embodiment, trend alert arrow 702 is pointing downwards to indicate a decrease in patient wellness. Display 700 is well-defined for ease of use by the clinician. In addition, display 700 provides information on the status of the alert condition, including but not limited to the time interval 703 and the parameter change 704, and a summary of information 705, such as but not limited to "$SPO_2$ has dropped rapidly in the last 20 minutes". In addition, other relevant information is displayed, such as the algorithm employed to determine the change in $SPO_2$ and its resultant alert condition.

Figure 8:
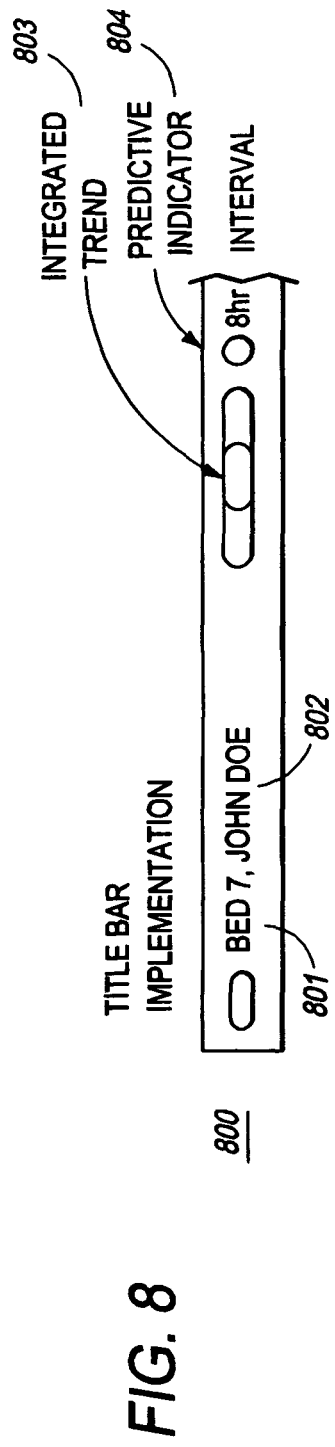
FIG. 8 depicts an integrated trend display of the patient monitoring system of the present invention, further illustrating a patient status title bar.

FIG. 8 depicts an integrated trend display of the patient monitoring system of the present invention, further illustrating a patient status title bar as shown at the central station. Patient status title bar 800 is also described with respect to FIGS. 2 and 3 above. The central station view comprises at least one, and preferably a plurality of patient status title bars 800. Patients are listed by bed number 801, name 802, and overall patient status. The overall patient status is indicated by integrated trend bar 803 that combines each measured patient parameter into an overall status indication and predictive model icon 804 that indicates overall patient status, as described above. In one embodiment, predictive model icon 804 is a predictive indicator dot.

Figure 9:
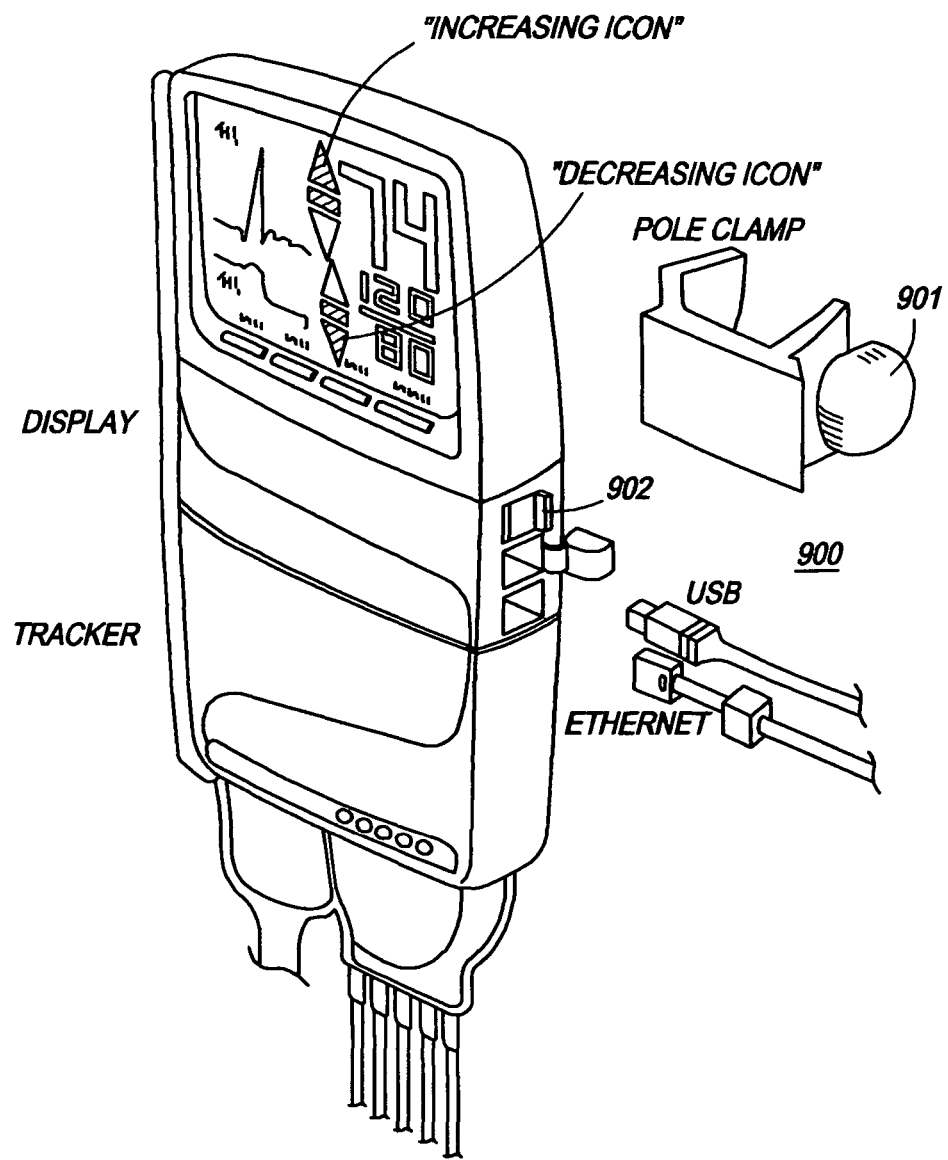
FIG. 9 depicts one embodiment of a bedside monitor patient information display of the present invention.

FIG. 9 depicts another embodiment of a bedside monitor patient information display of the present invention. More specifically, as shown in FIG. 9, in one embodiment, the patient bedside monitor may be handheld, portable unit 900. Optionally, handheld, portable monitor unit 900 may be a fixed unit when using pole clamp 901. Portable monitor unit 900 further comprises peripheral interface 902, allowing it to be linked to an external computing device such as a PC or a laptop. Data regarding a patient's condition may be transmitted to the computing device and stored for further processing, analysis and/or retrieval. The configuration of peripheral interface 902 may vary, depending upon the type of connection to the external computing device. For example, data may be transmitted from the bedside monitor to a PC over a wired link. Thus, peripheral interface 902 may comprise a USB port or RS232 serial connection for communication with the PC.

Additionally, bedside monitor 900 may optionally be equipped with the ability to transmit data by means of a wireless link, such as by radio waves or infrared. Thus, peripheral interface 902 may comprise a transmitter (not shown) capable of transmitting radio waves or an infrared signal to a computing device, which is configured to receive radio waves or an infrared signal. As shown in FIG. 9, bedside monitor 900 may optionally be placed in communication with other bedside monitors by including an Ethernet capability in peripheral interface 902. In this manner, all the bedside monitors, along with the central station may be interconnected into a high-speed local area network (LAN).

In addition to its use in the hospital and intensive care environments as described above, the patient monitoring system of the present invention may also be used to provide feedback to individuals engaged in exercise or physical activity. Such feedback is particularly useful for athletes and sportspersons, as it helps them in accurately measuring their progress. Two major parameters used for determining general health and physical fitness and monitoring optimal training levels are heart rate (in beats per minute) and the level of oxygen in blood. The physiological monitoring system of the present invention includes sensors for measuring heart rate and an oximeter for measuring blood oxygen level. Further, as described above with respect to FIG. 9, portable patient monitor unit 900 is suitable for use as a real time tracker that provides continuous feedback on the physiological parameters during the period of physical activity. For example, the display unit may be configured to be worn around a human user's waist, or may be configured to be mounted to a bicycle (e.g., mounted to the handlebars). The monitoring system may also be configured to display data on a treadmill display screen so that the monitoring system will provide heart rate and blood oxygen data for a subject walking or running on a treadmill. Irrespective of the location, the system has the ability to provide critical data and their analyses to the user at a single glance. The monitoring system also includes audible or visual alarms, which are activated when data for a physiological parameter does not meet a predetermined target. Thus, when a user's blood oxygen level or heart rate exceeds or falls short of a predetermined target, the user is instantly alerted. This is especially useful when a person is trying to achieve a particular fitness or training level.

Figure 10:
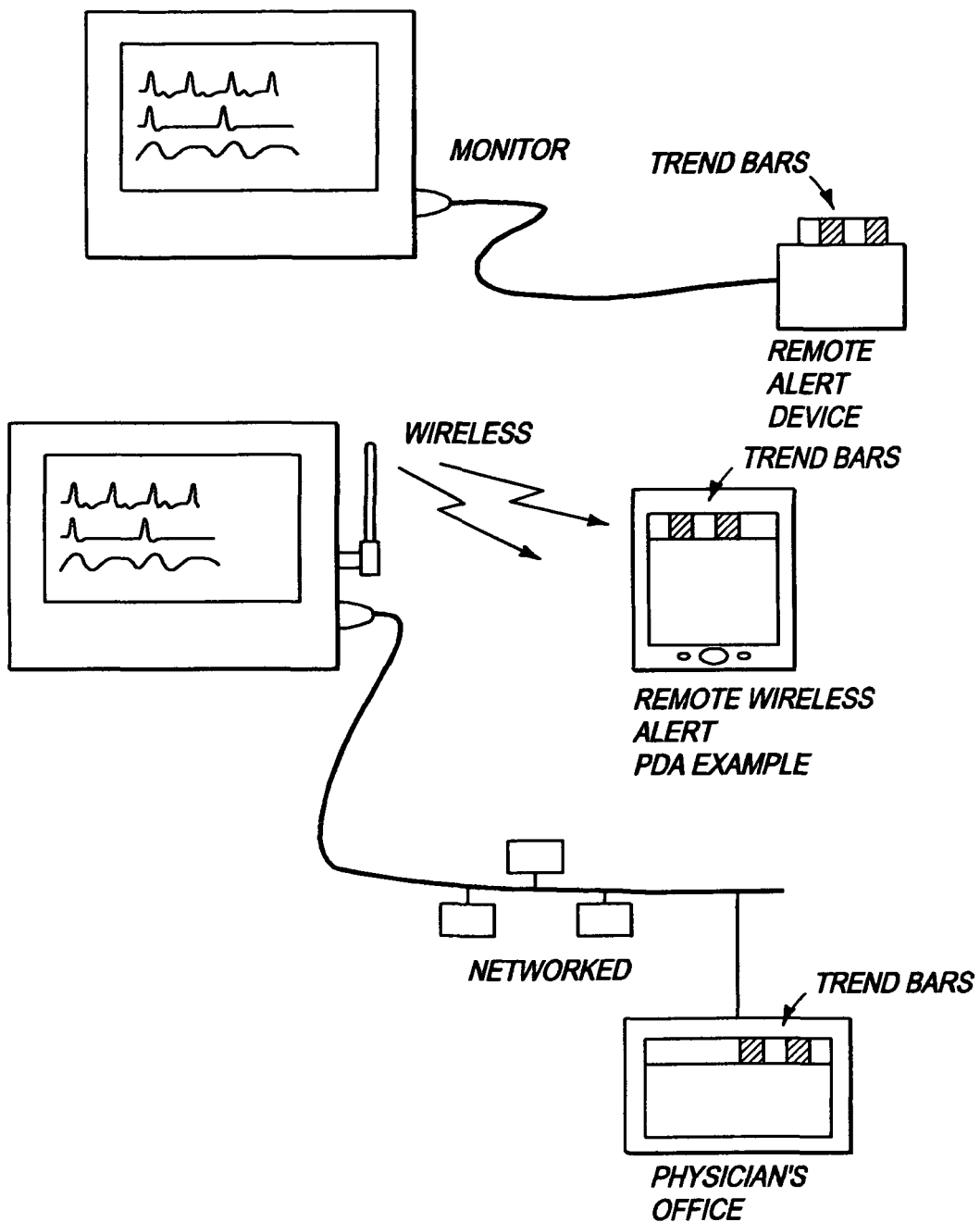
FIG. 10 is a diagram illustrating the interconnectivity and operation of the patient monitoring system with continuous trending display of the present invention, as employed in a clinical setting.

FIG. 10 is a diagram illustrating the interconnectivity and operation of patient monitoring system with continuous trending display of the present invention, as employed in a clinical setting. Thus, the continuous multi-parameter summary trending display wellness bar and predictive model "icon" are displayed via intensity or colors on a central display, a bedside monitor in the patient room, wireless devices, networked devices, and remote displays, depending on the needs and requirements of the clinical setting. Thus, patient status is always accessible by the clinician at a glance. For example, in one embodiment, referring back to FIG. 9, the multi-parameter summary bedside display is a portable, hand-held unit. The details of such unit have already been described with respect to FIG. 9 and will thus not be repeated herein.

Figure 11:
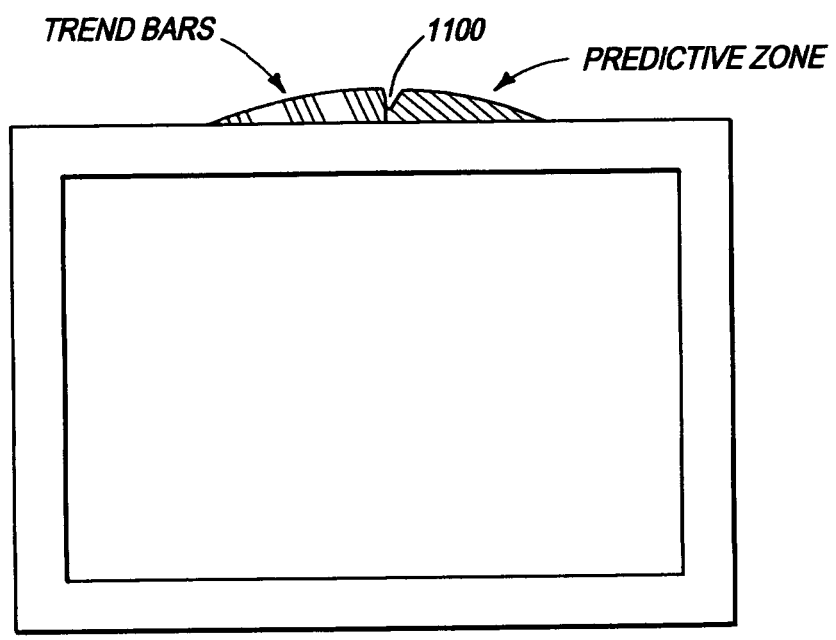
FIG. 11 is an illustration of a patient wellness trend bar as implemented on a nurse alert light.

FIG. 11 is an illustration of a patient wellness trend bar implemented as a clinician alert light, as described above. Referring back to FIG. 1, in one embodiment, monitor 102 further comprises a translucent bar that serves as a "nurse alert". Translucent bar 1100 comprises a series of LEDs (not shown) of different colors, such as but not limited to red, green and yellow. In one embodiment, the translucent bar is capable of displaying at least one or a plurality of colors to indicate the trending that is on the wellness bar. Thus, the translucent bar serves as a rough indicator of the wellness bar status of the patient, allowing a nurse or other clinician to easily glance into a patient room and access patient wellness status with respect to a combination of a plurality of physiological parameters. In particular, the translucent alert bar can be used in those situations where display areas are limited in scope, pixel size, and capability.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for monitoring the physiological condition of an individual, comprising:
(a) at least one $SpO_2$ sensor for measuring the individual's blood oxygen saturation level and providing data on said blood oxygen saturation level;
(b) at least one ECG sensor for measuring the individual's ECG heart rate and providing ECG data;
(c) a display unit coupled to the $SpO_2$ and ECG sensors and configured for displaying in real-time the blood oxygen saturation level and ECG data provided by said sensors;
(d) an inference engine executing on a computing device, wherein said computing device is coupled to said display unit, the $SpO_2$ sensor and the ECG sensor, wherein said inference engine uses the blood oxygen saturation level and ECG data to generate an indicator of the individual's health and transmits said indicator to the display unit, wherein said indicator comprises a bar of light comprising at least a first section and a second section wherein:
  (i) each of said first section and said second section provides a visual indication of the individual's health during a first time period and a second time period, respectively, wherein said first time period and said second time period are different;
  (ii) wherein, when said individual's health in said first time period differs from said individual's health in said second time period by an amount greater than a predetermined value, said first section is a different color than said second section,
  (iii) wherein selection of at least one of said first or second sections causes physiological parameter data used to determine the individual's health in said section to be displayed;

(iv) wherein selection of said indicator causes a plurality of rules governing how said visual indication of the individual's health is determined to be displayed; and (d) a central monitoring unit remote from said display unit and adapted for receiving said indicator.

2. A system for monitoring a physiological condition of an individual, comprising:

(a) at least one $SpO_2$ sensor for measuring the individual's blood oxygen saturation level and providing data on said blood oxygen saturation level;

(b) at least one ECG sensor for measuring the individual's ECG heart rate and providing ECG data;

(c) a display unit coupled to the $SpO_2$ and ECG sensors and configured for displaying in real-time the blood oxygen saturation level and ECG data provided by said sensors;

(d) an inference engine executing on a computing device, wherein said computing device is coupled to said display unit, the $SpO_2$ sensor and the ECG sensor, wherein said inference engine uses the blood oxygen saturation level and ECG data to generate an indicator of the individual's health and transmits said indicator to the display unit, wherein said indicator comprises a bar of light comprising at least a first section and a second section wherein:

(i) each of said first section and said second sections provides a visual indication of the individual's health during a first time period and a second time period, respectively, wherein said first time period and said second time period are different;

(ii) wherein, when said individual's health in said first time period differs from said individual's health in said second time period by an amount greater than a predetermined value, said first section is a different color intensity than said second section, and (iii) wherein selection of at least one of said first or second sections causes physiological parameter data used to determine the individual's health in said section to be displayed;

(d) a central monitoring unit remote from said display unit and adapted for receiving said indicator of the individual's health and physiological parameter.

3. A method for monitoring the physiological condition of an individual by displaying an indicator of the individual's health comprising the steps of:

(a) measuring the individual's blood oxygen saturation level with a $SpO_2$ sensor;

(b) providing data on said blood oxygen saturation level;

(c) measuring the individual's ECG heart rate with a ECG sensor;

(d) providing data on said individual's ECG heart rate;

(e) displaying in real-time the blood oxygen saturation level and ECG heart rate data provided by the sensors on a display unit;

(f) using the blood oxygen saturation level and ECG heart rate to generate the indicator of the individual's health wherein said indicator comprises a bar of light comprising at least a first section and a second section wherein:

(i) each of said first section and said second sections provides a visual indication of the individual's health during a first time period and a second time period, respectively, wherein said first time period and said second time period are different;

(ii) wherein, when said individual's health in said first time period differs from said individual's health in said second time period by an amount greater than a predetermined value, said first section is a different color than said second section, (iii) wherein selection of at least one of said first or second sections causes physiological parameter data used to determine the individual's health in said section to be displayed;

(iv) wherein selection of said indicator causes a plurality of rules governing how said visual indication of the individual's health is determined to be displayed; and (e) transmitting said indicator to the display unit;

(f) displaying said indicator on the display unit; and (g) receiving said indicator of the individual's health at a central monitoring station.

4. A system for monitoring a physiological condition of an individual, comprising:

(a) at least one $SpO_2$ sensor for measuring the individual's blood oxygen saturation level and providing data on said blood oxygen saturation level;

(b) at least one ECG sensor for measuring the individual's ECG heart rate and providing ECG data;

(c) a display unit coupled to the $SpO_2$ and ECG sensors and configured for displaying in real-time the blood oxygen saturation level and ECG data provided by said sensors;

(d) an inference engine executing on a computing device, wherein said computing device is coupled to said display unit, the $SpO_2$ sensor and the ECG sensor, wherein said inference engine uses the blood oxygen saturation level and ECG data to generate an indicator of the individual's health and transmits said indicator to the display unit, wherein said indicator comprises a vertical or horizontal bar of light comprising at least a first section and a second section wherein:

(i) each of said first section and said second sections provides a visual indication of the individual's health during a first time period and a second time period, respectively, wherein said first time period and said second time period are different;

(ii) wherein, when said individual's health in said first time period differs from said individual's health in said second time period by an amount greater than a predetermined value, said first section is a different color than said second section, (iii) wherein selection of at least one of said first or second sections causes physiological parameter data used to determine the individual's health in said section to be displayed;

(iv) wherein selection of said indicator causes a plurality of rules governing how said visual indication of the individual's health is determined to be displayed; and (d) a central monitoring unit remote from said display unit and adapted for receiving said indicator of the individual's health wherein said display unit and said central monitoring unit are configured to display overall individual status using a trend bar representing the combined status of blood oxygen saturation level and ECG data and an icon representing a prediction of the future combined status of blood oxygen saturation level and ECG data.

5. A system for monitoring a physiological condition of an individual, comprising:

(a) a plurality of sensors for measuring the individual's blood oxygenation level, blood pressure, ECG rate, and respiration rate and providing data on said blood oxygenation level, blood pressure, ECG rate, and respiration rate;

(b) a display unit coupled to the plurality of sensors and configured for displaying in real-time the blood oxygenation level, blood pressure, ECG rate, and respiration rate data provided by said plurality of sensors; and (c) an inference engine executing on a computing device, wherein said computing device is coupled to said display unit and the plurality of sensors, wherein said inference engine uses the blood oxygenation level, blood pressure, ECG rate, and respiration rate to generate an indicator of the individual's health wherein said indicator comprises a bar of light comprising at least a first section and a second section wherein:
  (i) each of said first section and said second sections provides a visual indication of the individual's health during a first time period and a second time period, respectively, wherein said first time period and said second time period are different;
  (ii) wherein, when said individual's health in said first time period differs from said individual's health in said second time period by an amount greater than a predetermined value, said first section is a different color than said second section,
  (iii) wherein selection of at least one of said first or second sections causes physiological parameter data used to determine the individual's health in said section to be displayed;
  (iv) wherein selection of said indicator causes a plurality of rules governing how said visual indication of the individual's health is determined to be displayed; and
(d) a central monitoring unit remote from said display unit and adapted for receiving said indicator of the individual's health.

6. A method for monitoring the physiological condition of an individual by displaying an indicator of the individual's health comprising the steps of:
  (a) measuring the individual's blood oxygenation level, blood pressure, ECG rate, and respiration rate with a plurality of sensors;
  (b) providing data on said individual's blood oxygenation level, blood pressure, ECG rate, and respiration rate;
  (c) displaying in real-time the individual's blood oxygenation level, blood pressure, ECG rate, and respiration rate provided by the plurality of sensors on a display unit;
  (d) using the blood oxygenation level, blood pressure, ECG rate, and respiration rate to generate the indicator of the individual's health wherein said indicator comprises a bar of light comprising at least a first section and a second section wherein:
    (i) each of said first section and said second sections provides a visual indication of the individual's health during a first time period and a second time period, respectively, wherein said first time period and said second time period are different;
    (ii) wherein, when said individual's health in said first time period differs from said individual's health in said second time period by an amount greater than a predetermined value, said first section is a different color than said second section;
    (iii) wherein selection of at least one of said first or second sections causes physiological parameter data used to determine the individual's health in said section to be displayed; and
    (iv) wherein selection of said indicator causes a plurality of rules governing how said visual indication of the individual's health is determined to be displayed;
  (e) transmitting said indicator to the display unit;
  (f) displaying said indicator on the display unit; and
  (g) receiving said indicator of the individual's general health at a central monitoring station.

* * * * *